United States Patent [19]

King

[11] Patent Number: 5,713,922

[45] Date of Patent: Feb. 3, 1998

[54] TECHNIQUES FOR ADJUSTING THE LOCUS OF EXCITATION OF NEURAL TISSUE IN THE SPINAL CORD OR BRAIN

[75] Inventor: Gary William King, Fridley, Minn.

[73] Assignee: Medtronic, Inc., Minneapolis, Minn.

[21] Appl. No.: 637,361

[22] Filed: Apr. 25, 1996

[51] Int. Cl.$^6$ .................................................. A61N 1/00
[52] U.S. Cl. ................................................ 607/2; 607/67
[58] Field of Search ................................. 607/2, 43, 45, 607/54, 58, 67, 72, 117, 118, 116, 139–141

[56] References Cited

U.S. PATENT DOCUMENTS

| | | | |
|---|---|---|---|
| 1,935,138 | 11/1933 | Windisch | 607/67 |
| 3,822,708 | 7/1974 | Zilber | 607/72 |
| 3,850,161 | 11/1974 | Liss . | |
| 3,918,461 | 11/1975 | Cooper | 607/45 |
| 5,002,053 | 3/1991 | Garcia-Rill et al. | 607/49 |
| 5,121,754 | 6/1992 | Mullett . | |
| 5,181,511 | 1/1993 | Nickolls et al. . | |
| 5,324,309 | 6/1994 | Kallok . | |
| 5,332,401 | 7/1994 | Davey et al. | 607/139 |
| 5,370,665 | 12/1994 | Hudrlik . | |

FOREIGN PATENT DOCUMENTS

WO 95/19804  7/1995  WIPO .

OTHER PUBLICATIONS

Holsheimer, et al., "Effects of Various Contact Combinations on Parathesia Coverage in Spinal Cord Stimulation", Institute for Biomedical Technology, Dept. Of Electrical Engineering, pp. 1–10.

Holsheimer, et al., "Effects of Electrode Geometry and Combination on Nerve Fibre Selectivity in Spinal Cord Stimulation", *Medical & Biomedical Engineering & Compt.*, vol. 33, pp. 676–682 (1995).

Holsheimer, et al., "Significance of the Spinal Cord Position in Spinal Cord Stimulation", [Supp] 64: 119–124.

Holsheimer, et al., "Contact Combinations in Epidural Spinal Cord Stimulation", *World Soc. For Stereotactic & Functional Neurosurgery*, pp. 220–233.

Holsheimer, et al., "How do Geometric Factors Influence Epidural Spinal Cord Stimulation?" *World Soc. For Stereotactic & Functional Neurosurgery*, pp. 234–249.

Deurloo et al., "Position Selective Activation of Peripheral Nerve Fibers", *Integrated Biomedical Engineering for Restoration of Human Function*, pp. 11–15(Feijen ed. 1995).

Deurloo et al., "Transverse Tripolar Stimulation for Selective FNS", IEEE Conference, Amsterdam (Nov. 1996).

Struijk et al., "Transverse Tripolar Spinal Cord Stimulation: Theoretical Performance of a Dual Channel System", *Medical & Biological Engineering & Computing*, pp. 273–279 (Jul. 1996).

*Primary Examiner*—William E. Kamm
*Assistant Examiner*—George R. Evanisko
*Attorney, Agent, or Firm*—Banner & Witcoff, Ltd.

[57] ABSTRACT

A method of controlling a volume of neural tissue stimulation with electrodes placed in the intraspinal tissue, on the surface of the brain or deep in the brain in which first, second and third electrodes are implanted in or adjacent to the desired neural tissue. Anode/cathode relationships are established between the electrodes and pulses are presented to the electrodes so that fibers or cell bodies in said neural tissue are activated. Amplitude and/or pulse width of the pulses are varied to steer the locus of cell body or axon activation.

41 Claims, 6 Drawing Sheets

TECHNIQUES FOR ADJUSTING THE LOCUS OF EXCITATION OF NEURAL TISSUE IN THE SPINAL CORD OR BRAIN

BACKGROUND OF THE INVENTION

1. Field of the Invention

This invention relates to means of stimulating neural tissue, and more particularly relates to means for adjusting the locus at which action potentials are induced in the brain, including electrode locations deep in the brain, near the surface of the brain, in the subdural spinal cord space or intraspinally.

2. Description of the Related Art

Two major practical problems reduce the efficacy of spinal cord stimulation (SCS) for pain control. One is the difficulty of directing the stimulation-induced paresthesia to the desired body part and the other is the problem of disagreeable sensations or motor responses to the stimulation, which reduce the comfortable amplitude range of the stimulation. It is generally agreed that in SCS for chronic pain, paresthesia should cover the whole pain region. With present stimulation methods and equipment, only highly skilled and experienced practitioners are able to position a stimulation lead in such a way that the desired overlap is reached and desired results are obtained over time with minimal side effects. It requires much time and effort to focus the stimulation on the desired body region during surgery, and it is difficult to redirect it afterwards, even though some readjustments can be made by selecting a different contact combination, pulse rate, pulse width or voltage. Repositioning of leads using surgery is sometimes required.

Redirecting paresthesia after surgery is highly desirable. Even if paresthesia covers the pain area perfectly during surgery, the required paresthesia pattern often changes later due to lead migration, or histological changes (such as the growth of connective tissue around the stimulation electrode) or disease progression. The problem of lead placement has been addressed by U.S. Pat. No. 5,121,754 by the use of a lead with a deformable distal shape. These problems are found with SCS, depth brain stimulation (DBS) and cortical surface stimulation.

A system capable of some adjustment of spinal cord excitation is described in PCT International Publication No. WO 95/19804, entitled "Multichannel Apparatus for Epidural Spinal Cord Stimulation" (Holsheimer et al., filed 24 Jan. 1994, published 27 Jul. 1995). However, that system is confined to the epidural space in the spinal column. The applicant has discovered that improved paresthesia is accomplished by special placing of electrodes and properly pulsing the electrodes inside the brain, over the cortical surface (supra- or subdurally), in the subdural spinal cord space or intraspinally.

SUMMARY OF THE INVENTION

The present invention can be used to advantage for altering the locus in neural tissue at which action potentials are induced by placing electrodes deep in the brain, near the brain or intraspinal tissue of the spinal column. According to a preferred embodiment, first, second and third electrodes are implanted near or within the neural tissue of interest. Anode/cathode relationships are established between the first, second and third electrodes. Electrical pulses are presented to each of the established anode/cathode relationships of the first, second and third electrodes. By using this technique, paresthesiae or desired motor or other effects can be created with a degree of precision unattainable by the prior art techniques.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
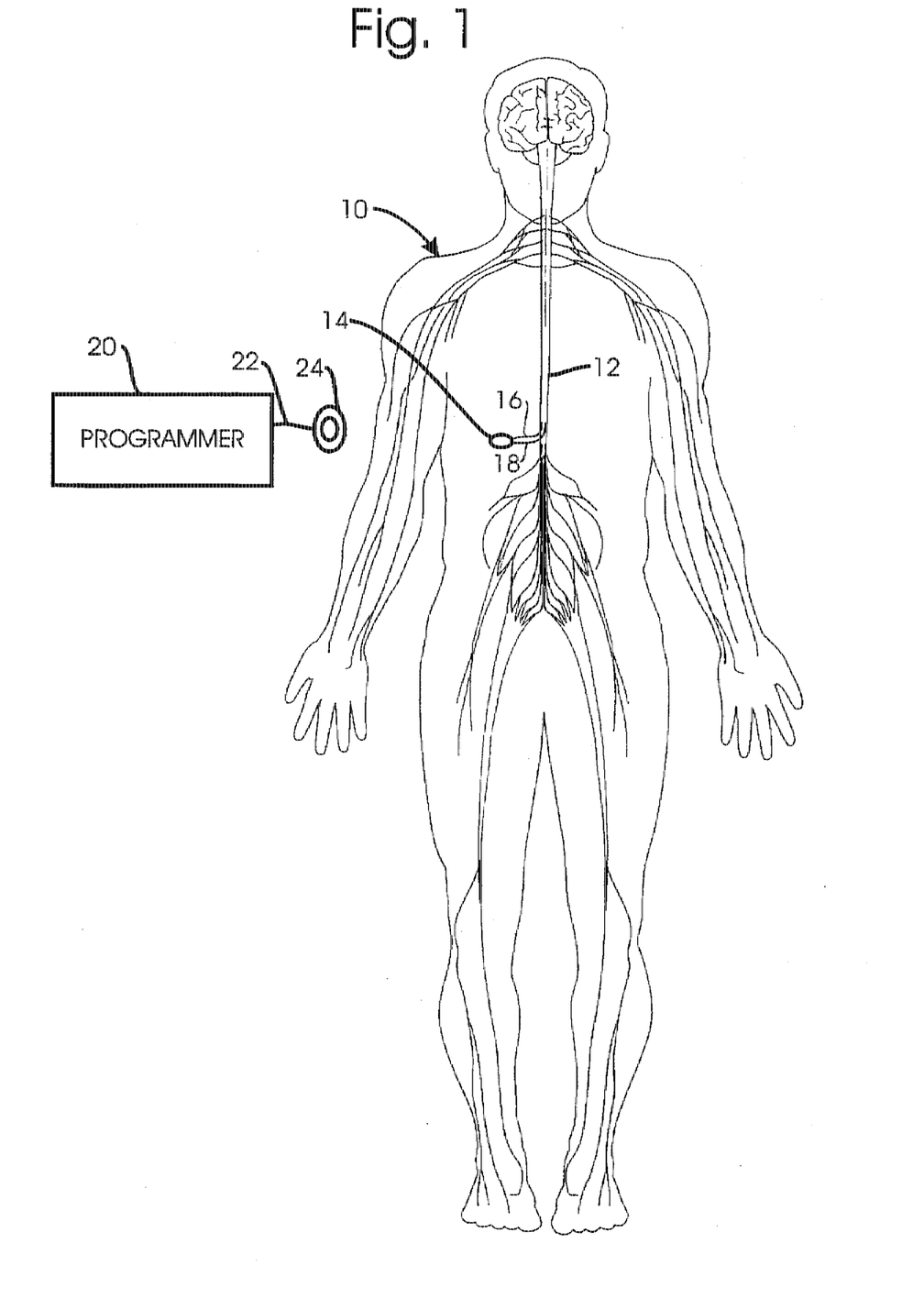
FIG. 1 is a diagrammatic view of a patient in which a preferred form of apparatus made in accordance with the invention has been implanted.
Figure 2:
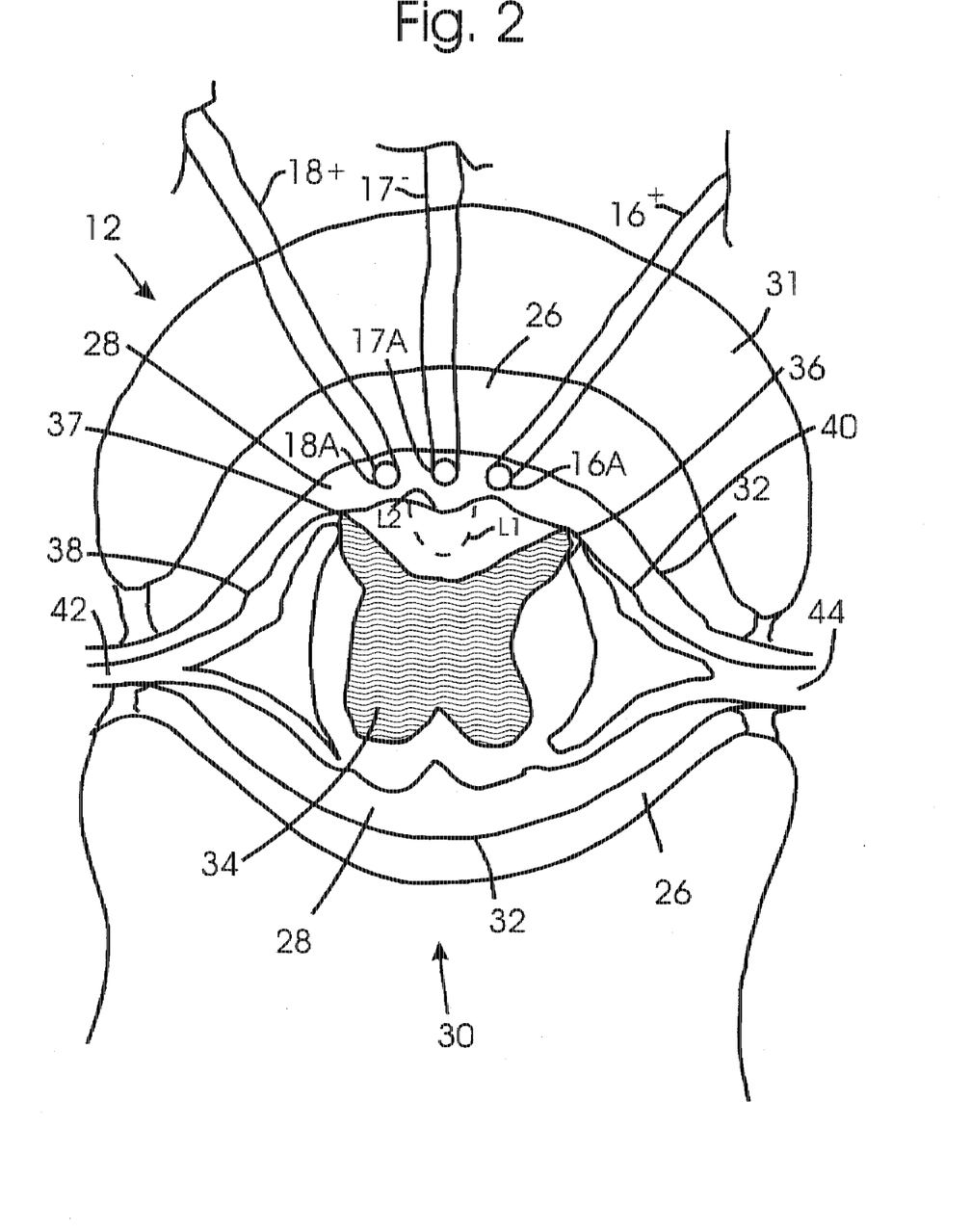
FIG. 2 is a cross-sectional view of an exemplary spinal column showing a typical position at which electrodes made in accordance with the preferred practice of the invention have been implanted in the subdural space and a locus of fiber activation.

FIG. 1 is a schematic view of a patient 10 having an implant of a neurological stimulation system employing a preferred form of the present invention to stimulate spinal cord 12 of the patient. The preferred system employs an implantable pulse generator 14 to produce a number of independent stimulation pulses which are sent to spinal cord 12 by insulated leads 16–18 coupled to the spinal cord by electrodes 16A–18A (FIG. 2). Electrodes 16A–18A also can be attached to separate conductors included within a single lead.

Implantable pulse generator 14 preferably is a modified implantable pulse generator available from Medtronic, Inc. under the trademark ITREL II with provisions for multiple pulses occurring either simultaneously or with one pulse shined in time with respect to the other, and having independently varying amplitudes and pulse widths. This preferred system employs a programmer 20 which is coupled via a conductor 22 to a radio frequency antenna 24. The system permits attending medical personnel to select the various pulse output options after implant using radio frequency communications. While the preferred system employs fully implanted elements, systems employing partially implanted generators and radio-frequency coupling may also be used in the practice of the present invention (e.g., similar to products sold by Medtronic, Inc. under the trademarks X-trel and Mattrix).

FIG. 2 is a cross-sectional view of spine 12 showing implantation of the distal end of insulated leads 16–18 which terminate in electrodes 16A–18A within subdural space 28 filled with cerebral spinal fluid. The electrodes may be conventional percutaneous electrodes, such as PISCES® model 3487A sold by Medtronic, Inc. Alternatively, electrodes 16A–18A may be constructed like electrical contacts 56, 58 and 60 shown in the above-identified PCT International Publication No. WO 95/19804 which is incorporated by reference (hereafter the "PCT Publication"). Also shown in FIG. 2 is a bony vertebral body 30, vertebral arch 31, and dura mater 32. The spine also includes gray matter 34, dorsal horns 36 and 37, dorsal roots 38 and 40, and peripheral nerves 42 and 44.

Still referring to FIG. 2, an anode/cathode relationship is established between electrodes 16A–18A in the manner described in the PCT Publication. For example, electrodes 16A and 18A are established as anodes (+) and electrode 17A is established as a cathode (−). Electrodes 16A–18A are placed in a generally planar configuration and are aligned along a common axis as shown and as taught in the PCT Publication. The electrodes could be placed on a flat or curved paddle, or they could be individually inserted in a percutaneous fashion. The electrodes are implanted near the dorsal surface of the spinal cord, under the dura mater.

Pulses are then applied to the electrodes as taught in the PCT Publication in order to redirect a locus of action potentials in nerve fibers in the spinal cord. The pulses may overlap in time and are independently variable in amplitude to best control the areas of activation, or they may also have independently variable pulse widths. The dotted line L1 shows the edge of a locus of excitation of nerve cells caused by pulses in electrodes 16A–18A. In this volume of tissue, L2, cells are depolarized beyond the threshold for production of action potentials. As shown in FIG. 2, when simultaneous pulses between electrode pairs 16A, 17A and between electrode pairs 17A, 18A are nearly equal in amplitude, volume L2 is nearly symmetrical about electrode 17A.

Figure 3:
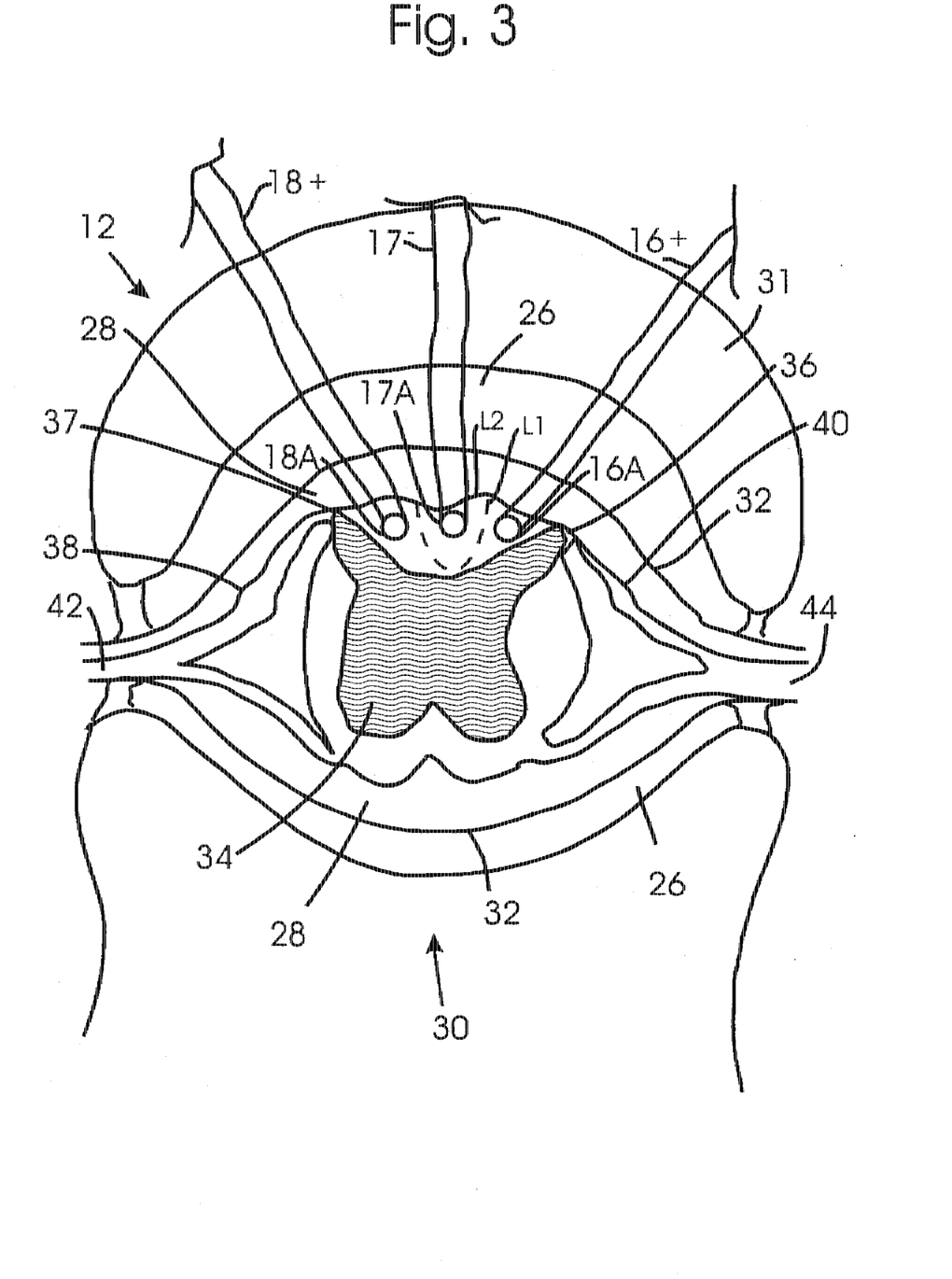
FIG. 3 is a cross-sectional view like FIG. 2 showing a locus of fiber activation in the intraspinal tissue due to implantation of electrodes in such location.

FIG. 3 illustrates the same configuration shown in FIG. 2, except that electrodes 16A–18A are implanted inside the spinal cord tissue. One or more of electrodes 16A–18A, especially the lateral ones, might be placed on the outer surface of the spinal cord. With balanced or equal amplitudes of simultaneous stimulation pulses, the locus of recruitment is nearly symmetrical about the cathode (i.e., electrode 17A). The electrodes should be inserted into the spinal cord with, for example, a percutaneous-type lead.

Figure 4:
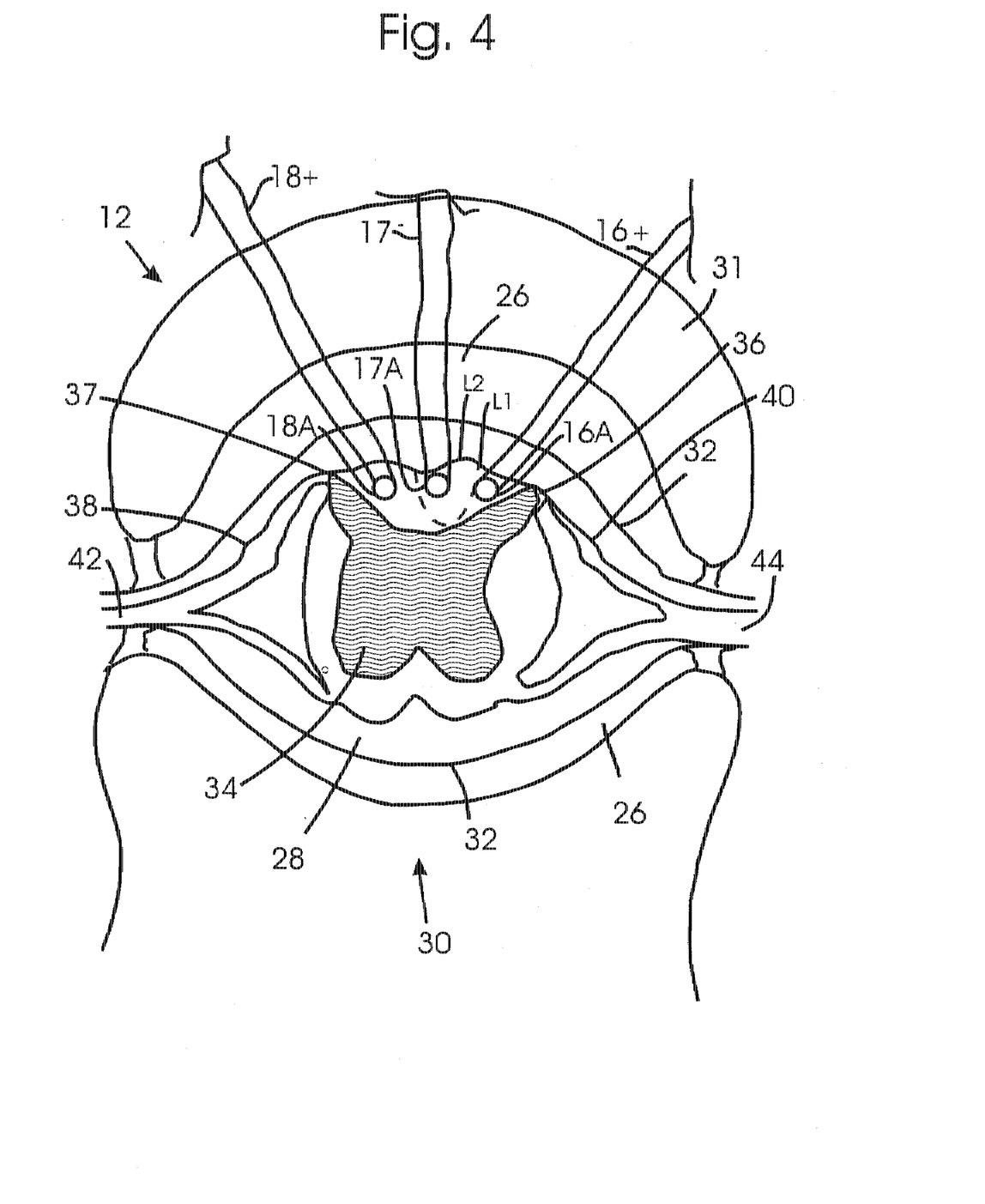
FIG. 4 is a view like FIG. 3 showing the locus of fiber activation in the intraspinal tissue due to a change in amplitude of the pulses applied to the electrodes compared to the amplitudes used in connection with FIG. 3.

FIG. 4 illustrates the same configuration shown in FIG. 3. However, the amplitude of the anodal pulse on electrode 18A has been increased in value, causing the locus of excitation L2 to shift away from that electrode. This is an unbalanced stimulation, and demonstrates the ability of this system to adjust the locus of excitation laterally by programming.

It also is possible to place the electrodes in a line that is parallel to the longitudinal axis of the spinal cord, and hence steer the locus of excitation rostrally or caudally. This could be used to activate certain dorsal roots over others, or affect certain spinal cord segments more than others.

Figure 5:
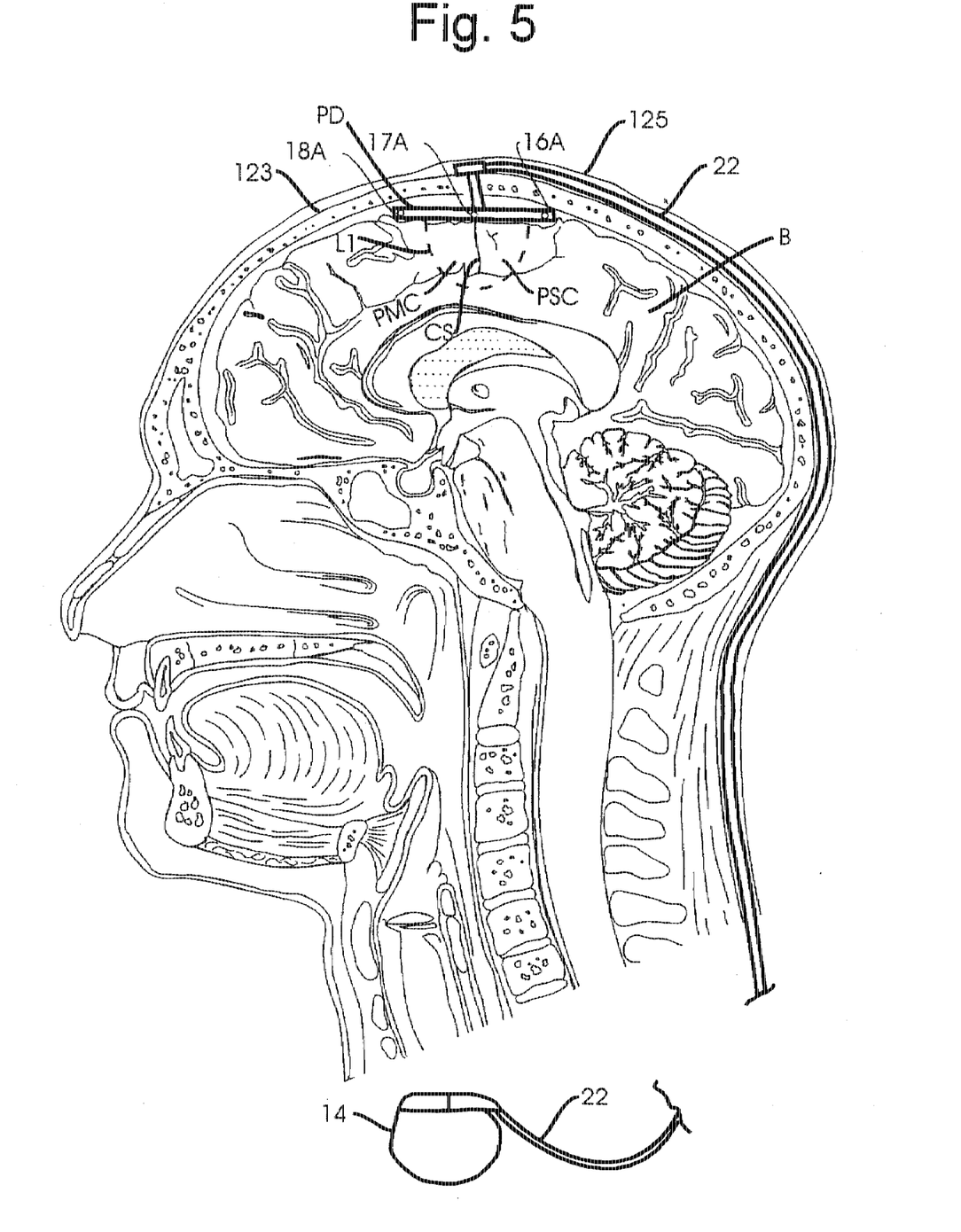
FIG. 5 is a cross-sectional view of the brain showing one form of placement of the electrodes of a preferred embodiment.

FIG. 5 illustrates cortical surface stimulation by electrodes 16A–18A that have been mounted on a paddle PD and implanted on the surface of the brain as shown. Pulses are supplied to the electrodes from device 14 over conductors 16–18 that are located within a cable 22 implanted between the scalp 125 and skull 123. The distal end of cable 22 is implanted in the brain through a hole in the skull by conventional stereotactic surgical techniques. Electrodes 16A–18A may be above the dura, or placed beneath the dura, in both cases accomplishing cortical surface stimulation.

In the center of the brain is a deep groove, called the central sulcus CS. Toward the anterior is the primary motor cortex PMC, consisting of neurons and axons that control motor movements on the opposite side of the body. Toward the posterior is the primary sensory cortex PSC. Generally, stimulation of the motor cortex causes discrete movements, and stimulation of the sensory cortex causes sensations, although effects may be mixed due to crossing, communicating axons. With the cathode 17A over the sulcus, and anodes both anteriorly (18A) and posteriorly (16A), the locus of excitation L2 may include both motor and sensory cortex as shown, or might, by steering, include only one or the other. The steering may be accomplished in the same manner described in connection with FIGS. 3 and 4. There is a somatotopic map of the body on both the primary motor cortex and the primary sensory cortex. It runs from medial to lateral, with the buttocks on the midline and top, the feet on the midline deep, and the back, arms, head, mouth and tongue progressively more lateral on the surface of the brain. If electrodes 16A, 17A and 18A are placed in a medial/lateral direction along this map (called a homunculus), or in a rostral/caudal direction along the part that goes deep into the brain, with steering of the electric fields, the paresthesia or motor event that is elicited can be moved to new body parts. This is another important application of this invention.

Figure 6:
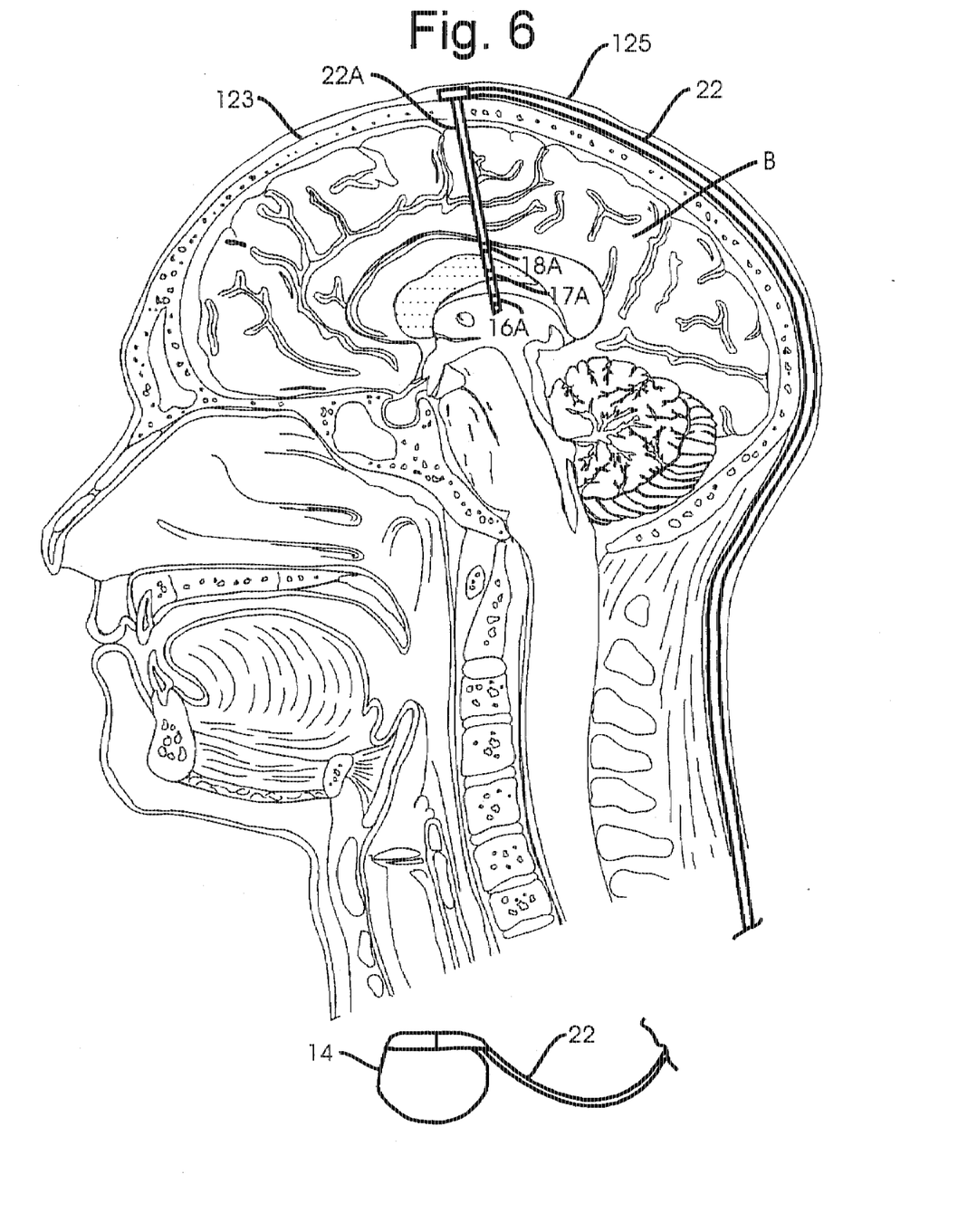
FIG. 6 is a view like FIG. 5 showing an alternative placement of the electrodes in the brain.

As shown in FIG. 6, electrodes 16A, 17A and 18A have been placed on a single lead 22A deep in the brain B. Alternatively, electrodes 16A, 17A and 18A could be placed deep in the brain on separate leads. By changing the amplitudes of pulses applied to the electrodes as illustrated in connection with FIGS. 3 and 4, the locus of excitation could be shifted along the axis of lead 22A. If the lead was not on a midline plane, or was in other deep brain sites, one, two or all three electrodes might be in brain tissue. In particular, DBS is done today to excite particular neural tissue elements of the thalamus, globus pallidus and other nuclear groups for the relief of chronic pain or to control movements. Sometimes the neural tissue elements to be excited (low frequency, less than 100 Hz) or inhibited (high frequency, greater than 100 Hz) are organized into thin sheets or lamina, e.g., the VIM thalamic nucleus. Other times, nearby groups of neurons or axons, e.g., the optic nerve, internal capsule, or medial lemniscus, are also in special orientations and groupings. It may be advantageous to avoid affecting them (e.g., preventing flashes of light effects) or deliberately to affect them (e.g., excite or inhibit axons of passage). Therefore, the precise location and orientation of the three electrodes is very important, and to be able to steer the fields along the generally coplanar axis of the three electrodes can be most beneficial. In addition, there are somatotopic maps of the body on the surface of the cerebellum, one in three dimensions in parts of the thalamus and also one in the dorsal column nuclei of the medulla. It would be advantageous to orient the lead relative to these maps, and to excite/inhibit groups of cell bodies or axons accordingly. In addition, lamina for visual fields are found in the lateral geniculate body, lamina for tones for hearing are found in the medial geniculate body, and maps of the retina are found in the occipital cortex. Hence, steering of excitation or inhibition by use of this invention can be most useful.

Those skilled in the art will recognize that the preferred embodiments may be altered and amended without departing from the true spirit and scope of the appended claims. For example, amplitude may refer to both voltage and current parameters, and non-rectangular wave pulses may be used with calculations of average pulse width.

I claim:

1. A method of controlling for therapeutic purposes a volume of neural tissue stimulation of a predetermined portion of a brain of a patient, the method comprising the steps of:

placing a first electrode, a second electrode, and a third electrode at least near said predetermined portion of the brain;

establishing anode/cathode relationships between said first electrode and said second electrode and between said first electrode and said third electrode; and presenting electrical pulses to each established anode/cathode relationship to cause a steerable locus of excitation of nerve fibers or cells of said brain;

whereby said nerve fibers or cells are activated in said predetermined portion of said brain.

2. A method, as claimed in claim 1, wherein said pulses overlap in time.

3. A method, as claimed in claim 1, further comprising the step of adjusting said electrical pulses whereby said volume of neural tissue stimulation is adjusted.

4. A method, as claimed in claim 1, wherein said pulses are independently variable in amplitude.

5. A method, as claimed in claim 1, wherein said pulses are variable in pulse width.

6. A method, as claimed in claim 1, wherein said first, second and third electrodes are placed in a generally planar configuration.

7. A method, as claimed in claim 1, wherein said first, second and third electrodes are placed generally along a common axis.

8. A method, as claimed in claim 1, wherein said predetermined portion is adjacent the central sulcus.

9. A method, as claimed in claim 1, wherein said predetermined portion is deep in the brain.

10. A method, as claimed in claim 1, wherein said predetermined portion is on the surface of said brain.

11. A method, as claimed in claim 1, wherein one or more of said electrodes are implanted in brain tissue, and others are in fluid spaces outside or inside the said brain tissue.

12. A method of controlling a volume of neural tissue stimulation of a predetermined portion of a brain of a patient, the method comprising the steps of:

placing a first electrode, a second electrode, and a third electrode at least near said predetermined portion of the brain:

establishing anode/cathode relationships between said first electrode and said second electrode and between said first electrode and said third electrode: and presenting electrical pulses to each established anode/cathode relationship, whereby nerve fibers or cells are activated in said predetermined portion of said brain and wherein said pulses are independently variable in amplitude.

13. A method, as claimed in claim 12, wherein said pulses are variable in pulse width.

14. A method, as claimed in claim 12, wherein said step of placing includes placing said first electrode, said second electrode, and said third electrode in a generally planar configuration.

15. A method, as claimed in claim 12, wherein said step of placing includes placing said first electrode, said second electrode, and said third electrode generally along a common axis.

16. A method, as claimed in claim 12, wherein said predetermined portion is adjacent the central sulcus.

17. A method, as claimed in claim 12, wherein said predetermined portion is deep in the brain.

18. A method, as claimed in claim 12, wherein said predetermined portion is on the surface of said brain.

19. A method, as claimed in claim 12, wherein said step of placing includes placing at least one of said electrodes in brain tissue, and includes placing other electrodes in fluid spaces outside or inside said brain tissue.

20. A method, as claimed in claim 12, further comprising the step of adjusting said electrical pulses whereby said volume of neural tissue stimulation is adjusted.

21. A method of controlling a volume of neural tissue stimulation of a predetermined portion of a brain of a patient, the method comprising the steps of:

placing a first electrode, a second electrode, and a third electrode at least near said predetermined portion of the brain:

establishing anode/cathode relationships between said first electrode and said second electrode and between said first electrode and said third electrode; and presenting electrical pulses to each established anode/cathode relationship, whereby nerve fibers or cells are activated in said predetermined portion of said brain and wherein said pulses are variable in pulse width.

22. A method, as claimed in claim 21, wherein said step of placing includes placing said first electrode, said second electrode, and said third electrode in a generally planar configuration.

23. A method, as claimed in claim 21, wherein said step of placing includes placing said first electrode, said second electrode, and said third electrode generally along a common axis.

24. A method, as claimed in claim 21, wherein said predetermined portion is adjacent the central sulcus.

25. A method, as claimed in claim 21, wherein said predetermined portion is deep in the brain.

26. A method, as claimed in claim 21, wherein said predetermined portion is on the surface of said brain.

27. A method, as claimed in claim 21, wherein said step of placing includes placing at least one of said electrodes in brain tissue, and includes placing other electrodes in fluid spaces outside or inside said brain tissue.

28. A method, as claimed in claim 21, further comprising the step of adjusting said electrical pulses whereby said volume of neural tissue stimulation is adjusted.

29. A method of controlling a volume of neural tissue stimulation of a predetermined portion of a brain of a patient, the method comprising the steps of:

placing a first electrode, a second electrode, and a third electrode at least near said predetermined portion of the brain;

establishing anode/cathode relationships between said first electrode and said second electrode and between said first electrode and said third electrode:

presenting electrical pulses to each established anode/cathode relationship whereby nerve fibers or cells are activated in said predetermined portion of said brain and wherein said step of placing includes placing said first electrode, said second electrode, and said third electrode in a generally planar configuration.

30. A method of controlling a volume of neural tissue stimulation of a predetermined portion of a brain of a patient, the method comprising the steps of:

placing a first electrode, a second electrode, and a third electrode at least near said predetermined portion of the brain:

establishing anode/cathode relationships between said first electrode and said second electrode and between said first electrode and said third electrode; and presenting electrical pulses to each established anode/cathode relationship, whereby nerve fibers or cells are activated in said predetermined portion of said brain and wherein said step of placing includes placing said first electrode, said second electrode, and said third electrode generally along a common axis.

31. A method of controlling a volume of neural tissue stimulation of a predetermined portion of a brain of a patient, the method comprising the steps of:

placing a first electrode, a second electrode, and a third electrode at least near said predetermined portion of the brain;

establishing anode/cathode relationships between said first electrode and said second electrode and between said first electrode and said third electrode; and presenting electrical pulses to each established anode/cathode relationship, whereby nerve wherein said predetermined in said predetermined portion of said brain and wherein said predetermined portion is adjacent the central sulcus.

32. A method of controlling a volume of neural tissue stimulation of a predetermined portion of a brain of a patient, the method comprising the steps of:

placing a first electrode, a second electrode, and a third electrode at least near said predetermined portion of the brain;

establishing anode/cathode relationships between said first electrode and said second electrode and between said first electrode and said third electrode; and presenting electrical pulses to each established anode/cathode relationship;

whereby nerve fibers or cells are activated in said predetermined portion of said brain and wherein said predetermined portion is deep in the brain.

33. A method of controlling a volume of neural tissue stimulation of a predetermined portion of a brain of a patient, the method comprising the steps of:

placing a first electrode, a second electrode, and a third electrode at least near said predetermined portion of the brain;

establishing anode/cathode relationships between said first electrode and said second electrode and between said first electrode and said third electrode; and presenting electrical pulses to each established anode/cathode relationship.

whereby nerve fibers or cells are activated in said predetermined portion of said brain wherein said predetermined portion is on the surface of said brain.

34. A method of controlling a volume of neural tissue stimulation of a predetermined portion of a brain of a patient, the method comprising the steps of:

placing a first electrode, a second electrode, and a third electrode at least near said predetermined portion of the brain;

establishing anode/cathode relationships between said first electrode and said second electrode and between said first electrode and said third electrode; and presenting electrical pulses to each established anode/cathode relationship, whereby nerve fibers or cells are activated in said predetermined portion of said brain and wherein said step of placing includes placing at least one of said electrodes in brain tissue, and includes placing other electrodes in fluid spaces outside or inside said brain tissue.

35. A method of controlling a volume of neural tissue stimulation of a predetermined portion of a brain of a patient, the method comprising the steps of:

placing a first electrode, a second electrode, and a third electrode in a subdural area of said brain;

establishing anode/cathode relationships between said first electrode and said second electrode and between said first electrode and said third electrode; and presenting electrical pulses to each established anode/cathode relationship to cause a steerable locus of excitation of nerve fibers or cells of said subdural area of said brain, whereby said nerve fibers or cells are activated in said subdural area of said brain.

36. A method, as claimed in claim 35, wherein said pulses overlap at least partially in time.

37. A method, as claimed in claim 35, wherein said pulses are independently variable in amplitude.

38. A method, as claimed in claim 35, wherein said pulses are variable in pulse width.

39. A method, as claimed in claim 35, wherein said step of placing includes placing said first electrode, said second electrode, and said third electrode in a generally planar configuration.

40. A method, as claimed in claim 35, wherein said step of placing includes placing said first electrode, said second electrode, and said third electrode generally along a common axis.

41. A method, as claimed in claim 35, further comprising the step of adjusting said electrical pulses whereby said volume of neural tissue stimulation is adjusted.

* * * * *

UNITED STATES PATENT AND TRADEMARK OFFICE
CERTIFICATE OF CORRECTION

PATENT NO. : 5,713,922
DATED : February 3, 1998
INVENTOR(S) : Gary William King

It is certified that error appears in the above-identified patent and that said Letters Patent is hereby corrected as shown below:

Column 6, Claim 29, line 50 reads "said first electrode and said third electrode:" and should read --said first electrode and said third electrode: and--

Column 7, Claim 31, line 20 reads "whereby nerve wherein said predetermined in said pre-" and should read --whereby nerve fibers or cells are activated in said pre- --

Column 7, Claim 33, line 50 reads "termined portion of said brain wherein said predeter-" and should read --termined portion of said brain and wherein said predeter- --

Signed and Sealed this

Nineteenth Day of January, 1999

Attest:

Attesting Officer

*Acting Commissioner of Patents and Trademarks*